United States Patent [19]

Mathew et al.

[11] Patent Number: 4,551,324

[45] Date of Patent: * Nov. 5, 1985

[54] PREPARATION FROM HYDROXYLAMMONIUM SULFATE OF OTHER HYDROXYLAMMONIUM SALTS VIA ALCOHOLIC HYDROXYLAMINE

[75] Inventors: Chempolil T. Mathew, Randolph; Harry E. Ulmer, Morristown, both of N.J.

[73] Assignee: Allied Corporation, Morris Township, Morris County, N.J.

[*] Notice: The portion of the term of this patent subsequent to Mar. 26, 2002 has been disclaimed.

[21] Appl. No.: 534,292

[22] Filed: Sep. 23, 1983

Related U.S. Application Data

[63] Continuation-in-part of Ser. No. 437,920, Nov. 1, 1982.

[51] Int. Cl.$^4$ ............................................. C01B 21/20
[52] U.S. Cl. .................................... 423/387; 423/545; 423/551
[58] Field of Search ...................... 423/387, 545, 551

[56] References Cited

U.S. PATENT DOCUMENTS

| | | |
|---|---|---|
| 2,346,665 | 4/1944 | Cupery . |
| 2,397,508 | 4/1946 | Rouault . |
| 2,483,252 | 9/1949 | Tryon . |
| 3,145,082 | 8/1964 | Rausch et al. ................ 423/387 |
| 3,936,494 | 2/1976 | Lipowski . |
| 4,147,623 | 4/1979 | Koff et al. ..................... 423/387 |
| 4,507,248 | 3/1985 | Mathew et al. ................ 423/387 |

FOREIGN PATENT DOCUMENTS 1247284  8/1967  Fed. Rep. of Germany ...... 423/387

OTHER PUBLICATIONS

Feiser, *Introduction to Organic Chemistry*, (1957), D. C. Heath and Co., pp. 96, 97.

Kirk-Othmer, *Encyclopedia of Chemical Technology*, Second Edition, (1967), Interscience Publishers, pp. 494-496, vol. 11.

*Primary Examiner*—John Doll
*Assistant Examiner*—Wayne A. Langel
*Attorney, Agent, or Firm*—Richard C. Stewart; Gerhard H. Fuchs

[57] ABSTRACT

Solid hydroxylammonium sulfate is reacted with an alcohol solution of an alkali metal hydroxide or alkoxide to produce an alcoholic hydroxylamine liquid phase and a sulfate-containing solid phase. The liquid phase is further reacted with an acid other than sulfuric acid to form another hydroxylammonium salt. The different bases behave differently with regard to suitable and preferably solvents and temperatures.

30 Claims, No Drawings

PREPARATION FROM HYDROXYLAMMONIUM SULFATE OF OTHER HYDROXYLAMMONIUM SALTS VIA ALCOHOLIC HYDROXYLAMINE

DESCRIPTION

This is a continuation-in-part of U.S. 437,920, filed Nov. 1, 1982.

BACKGROUND OF THE INVENTION

Hydroxylamine, usually in the form of salts such as hydroxylammonium sulfate, hydroxylammonium chloride or the like is widely used as a reagent for preparing various industrial, specialty and pharmaceutical chemicals. Many products containing oxime or substituted hydroxylamine groups are not susceptible to production in aqueous media. Accordingly, such materials are normally prepared by reaction of solutions of hydroxylammonium chloride in organic solvents such as methanol with the organic precursor in the presence of sufficient base to neutralize the by-product HCl. Because hydroxylammonium sulfate (also called hydroxylamine sulfate) is not soluble in methanol, however, the cheaper sulfate reagent cannot be used to prepare these materials. Many other hydroxylammonium salts are more difficult to prepare than the sulfate (made by the Raschig process) and therefore would desirably be made from the sulfate. Proposals to do so in an ion exchange, exclusion or extraction column process are contained in U.S. Pat. Nos. 4,166,842 to Tunick et al., 4,147,623 to Koff et al and 4,202,765 to Koff et al.

Hydroxylammonium salts of organic acids are made in U.S. Pat No. 2,483,252 to Tryon (1949) by reaction of hydroxylammonium sulfate or chloride with ammonium or alkali metal salts of such acid, added as such or made in situ, with the reaction temperature usually 40°-70° C. (see col. 2, lines 1-37).

BRIEF DESCRIPTION OF THE INVENITON

A process has been discovered which enables solid hydroxylammonium sulfate to be used to provide hydroxylamine values in alcoholic solutions and to produce other hydroxylammonium salts therefrom. Accordingly, the present invention includes a process comprising the steps:

(a) reacting an alcoholic solution of a base selected from the group consisting of sodium hydroxide, potassium hydroxide, lithium hydroxide, ammonium hydroxide and the corresponding alkoxides of 1-5 carbons with solid hydroxylammonium sulfate, employing an alcohol of 1-3 carbons, a temperature, a pressure and a time sufficient to produce a liquid phase having at least 50% of the hydroxylamine values of the hydroxylammonium sulfate, (b) separating the solid phase comprising a sulfate salt corresponding to said base from the liquid phase. and (c) reacting the liquid phase with an acid other than sulfuric acid to produce an hydroxylammonium salt other than hydroxylammonium sulfate.

In the simplest form, this process produces an alcoholic solution of free hydroxylamine with little or no water content (depending upon the base used) and a by-product solid phase containing sulfate salts. Depending, however, upon how much base is used, the alcoholic solution produced may be more or less basic than free hydroxylamine. The alcoholic solution is converted to various salts, including hydroxylammonium chloride and hydroxylammonium nitrate, after separation of the solid phase.

For preparing hydroxylammonium salts of organic acids, however, the present invention also comprises a process comprising the steps:

(a) reacting an alcoholic solution of a base or basic organic salt selected from the group consisting of sodium hydroxide, potassium hydroxide, lithium hydroxide, ammonium hydroxide, the corresponding alkoxides of 1-5 carbons and the corresponding organic salts with solid hydroxylammonium sulfate and, in the case of base, an organic acid, in the substantial absence of added water or water introduced with the alcohol; employing an alcohol of 1-3 carbons, a temperature not greater than about 30° C., a pressure and a time sufficient to produce a liquid phase having at least 50% of the hydroxylamine values of the hydroxylammonium sulfate and a solid alkali metal or ammonium sulfate corresponding to the base or basic salt; and (b) separating the solid phase comprising sulfate salt from a liquid phase containing an organic hydroxylammonium salt corresponding to said basic organic salt or organic acid, said liquid phase being substantially free of sulfate.

DETAILED DESCRIPTION OF THE INVENTION

Four materials used in the process of the present invention are a base, an alcohol solvent, hydroxylammonium sulfate and an acid corresponding to the desired product salt. The hydroxylammonium sulfate is normally in solid form, preferably divided up into relatively fine powder or crystals, and may be produced in a variety of processes including, especially, that described in U.S. Pat. No. 4,349,520 of Bonfield et al. (Sept. 14, 1982). The alcohol may be any alkanol of 1-3 carbons, and especially methanol or ethanol, but also isopropanol and propanol when the base is an alkoxide. The base may be sodium hydroxide, potassium hydroxide, lithium hydroxide, ammonium hydroxide or an alkoxide. Suitable alkoxides are those of 1-4 carbons such as methoxides, ethoxides, isopropoxides, propoxides and butoxides of sodium, potassium or lithium. It is contemplated, however, that for any particular base, not all alcohols are suitable. Furthermore, for any particular base, specified conditions of temperature and/or pressure may be necessary of achieve the desired conversion of at least about 50% of the hydroxylamine values from the solid hydroxylammonium sulfate to the liquid phase. The acid may be any organic or inorganic acid other than sulfuric acid.

In the case of sodium hydroxide as base, any of the alcohols indicated above may be used as solvent. The preferred solvent for use with sodium hydroxide is methanol, with ethanol being slightly less preferred. It has been found that for both methanol and ethanol as solvent, the process of the present invention proceeds to higher conversions at lower temperatures. Thus the reaction temperature, while it may be as high as about 30° C., is preferably no greater than about 20° C. and more preferably no greater than about 10° C. Comparative Example 3, below, illustrates the significantly lower yields obtained at 35°-40° C. compared to those obtained at 22°-25° C. (e.g., Example 2) and at 5°-10° C. (e.g., Example 1). The concentration of sodium hydroxide in methanol or ethanol is not critical, but it is preferred to operate as near to the solubility limit of sodium hydroxide in the alcoholic solvent as possible without creating so viscous a solution that agitation becomes difficult. Larger amounts of the solvent may also be used if tolerable in subsequent reactions. Various of the examples illustrate the use of relatively concentrated methanolic and ethanolic solutions of sodium hydroxide in the present process. The amount of sodium hydroxide should be at least that required to neutralize 50% of the hydroxylammonium sulfate reacted, preferably at least that necessary to neutralize all of the hydroxylammonium sulfate. It is contemplated that greater amounts of sodium hydroxide than that stoichiometrically required may be used and, as indicated in Example 9 below, such excess sodium hydroxide may increase the reaction rate without detracting from reaction yields. Excess sodium hydroxide is normally to be used, however, only if the product alcoholic solution is to be used as a reagent in processes where more base would normally be charged at a later time. In other cases, the excess base can be neutralized before the solution is used further. Thus, the product solution can be formed at any desired pH such as from 5 to 12.

In using sodium hydroxide in ethanol as the solvent, lower temperatures are still preferred, with reaction below about 30° C., preferably below about 20° C. and more preferably no greater than about 10° C. being contemplated. It appears, however, that the reaction in ethanol is less temperature dependent than the reaction in methanol (see Examples 11 and 12 below).

Potassium hydroxide behaves quite differently from sodium hydroxide in the process of the present invention. First, methanol is not a suitable solvent for use with potassium hydroxide. As indicated in Comparative Examples 15 and 16 below, reaction of potassium hydroxide in methanol with hydroxylammonium sulfate produces extremely low yields either at 10° C. or at 22°–25° C. As indicated in Examples 17 and 18 below, however, potassium hydroxide in ethanol is a highly effective means of conducting the present process. These examples demonstrate that the reaction of potassium hydroxide in ethanol with hydroxylammonium sulfate proceeds at a slightly greater rate and to a slightly greater conversion at 22°–25° C. than at 5°–10° C. Accordingly, any temperature not greater than about 40° C. (preferably not greater than 30° C.) may be used with potassium hydroxide as the base, with temperatures of about 15 to about 25° C. being preferred. Temperatures above 40° C. should not normally be employed, however, since the product free hydroxylamine is likely to decompose significantly faster at such temperatures. As in the case of sodium hydroxide, potassium hydroxide may be used at any concentration and in any amount relative to the hydroxylammonium sulfate charged. Again, however, it is preferred in many cases to use a saturated or nearly saturated solution of potassium hydroxide in ethanol rather than a dilute solution. It is also preferred to use, relative to the stoichiometric amount of potassium hydroxide, at least that needed to neutralize 50% of the hydroxylammonium sulfate, preferably at least that necessary to neutralize all of the hydroxylammonium sulfate. Excesses of potassium hydroxide may also be used.

Lithium hydroxide, as a base in the present invention, may be used with methanol or ethanol. The reaction appears to proceed to slightly higher conversions at higher temperatures, as indicated by Examples 13 and 14 below. Nevertheless, any temperature up to about 40° C. may be use, with a range of about 10 about 40° C. being preferred, and a range of about 15 to about 25° being more preferred. The reaction of lithium hydroxide in methanol appears to proceed at a slower rate and/or to a lower final conversion than either the reaction of sodium hydroxide in methanol or ethanol or the reaction of potassium hydroxide in ethanol. The above comments relating to concentration of base in the alcohol and to amounts of base relative to hydroxylammonium sulfate made in respect to sodium hydroxide and potassium hydroxide apply equally to lithium hydroxide.

While isopropanol or propanol may be used as solvents with NaOH, KOH or LiOH, the limited solubilities of these hydroxides and of the product hydroxylamine in these solvents makes these embodiments less preferred to those described above.

Ammonium hydroxide, as a base, may be used with any of the lower alcohols in a manner similar to that employed with lithium hydroxide. The term "ammonium hydroxide" is intended to include ammonia plus some amount of water, such as equimolar amounts of ammonia and water, or half or twice the equimolar amount of water. Using ammonia without any water is not considered satifactory, based on the poor yields shown in comparative Examples 20–24, below.

In using sodium hydroxide, potassium hydroxide or lithium hydroxide, pressure is not a critical factor since neither the base nor the solvent is very volatile. Only when ammonia is used, is pressure at all a factor, and even then atmospheric or even pressures below atmospheric may be used, but pressures at or above atmospheric pressure are preferred, and atmospheric pressure is more preferred.

Alkoxides such as sodium methoxide, ethoxide, isopropoxide, propoxide, butoxide and pentylate may be used in place of the hydroxides, having the advantage of not producing water as by-product. Therefore, when a substantially water-free hydroxylamine solution is desired, these more expensive alkoxide bases should be used. Normally, the solvent will correspond to the anion (e.g., sodium methoxide in methanol), but mixed systems (e.g., sodium butoxide in methanol) may be used if the solvent later present (after the hydroxylamine-consuming reaction) is not to be recovered and recycled or can be distilled. While the anion may be larger than three carbons, the solvent is normally a 1–3 carbon alkanol (and is preferably methanol or ethanol) because free hydroxylamine is more soluble in these lower alkanols. If the product hydroxylammonium salt is organic (e.g. the acetate) and the anion is present initially (e.g. by reacting sodium acetate), then the solubility of free hydroxylamine becomes less critical and higher alcohol solvents, e.g. isopropanol or n-propanol, become more suitable.

In similar fashion, the alkoxides of lithium and potassium may be used, except that potassium alkoxides would normally not be used with methanol as solvent.

Alkoxides are more expensive than hydroxides and are, therefore, normally not used unless the 3% or so water in the product solution of the above reactions of hydroxides cannot be tolerated for a particular use. The present invention, using alkoxides, still makes available the use of hydroxylammonium sulfate for such water-sensitive uses.

In each case, one preferred mode of conducting the reaction is to first dissolve (or slurry) the base in the alcohol and then react the alcoholic solution with hydroxylammonium sulfate. As illustrated by Examples 1 and 8, below, essentially identical results can be achieved either by adding the solid hydroxylammonium sulfate to the alcoholic solution or by adding the alcoholic base to the solid hydroxylammonium sulfate. Furthermore, it is contemplated that the two may be mixed in any conventional batch or continuous process scheme normally used to react a solid with a liquid. A less preferred method of conducting the present invention is to mix the base (solid or gas) with the hydroxylammonium sulfate first, and then to add the alcohol. This scheme is less preferred because the process of dissolving the base in the alcohol (which is required before the reaction can occur) is normally an exothermic reaction. Since high temperatures are generally not required (and in the case of sodium hydroxide are preferably avoided), it is desirable that the act of dissolving base in alcohol be conducted first, that the alcoholic solution be cooled and that the cooled alcoholic solution be reacted with the hydroxylammonium sulfate. Another less preferred method is to add the base slowly to hydroxylammonium sulfate slurried in alcohol.

Once the reaction between alcoholic base and hydroxylammonium sulfate is complete, or while it is proceeding, the alcoholic solution containing hydroxylamine values is further reacted with either a mineral acid (inorganic acid) or an organic acid. In one mode, this reaction is conducted after separating the by-product sulfate (e.g., sodium sulfate) from the alcoholic hydroxylamine solution. Thus, as illustrated in certain Examples below, the separated hydroxylaminecontaining liquid phase is reacted with acids such as HCl, nitric acid, phosphoric acid, perchloric acid, oxalic acid, acetic acid, formic acid or benzoic acid to produce the corresponding hydroxylammonium salt (e.g., hydroxylammonium chloride, hydroxylammonium nitrate, dihydroxylammonium oxalate or trihydroxylammonium phosphate). In addition to these acid exemplified, one can use, for example, arsenic acid, fluoboric acid, propronic acid, toluenesulfonic acid, benzenesulfonic acid. In general, because of the ease of reacting alcoholic hydroxylamine solutions, any such acid can be used even if the product is slightly unstable, such as is the case for the formate, nitrate and perchlorate. Excess base may be removed by neutralizing to pH 7-9 before separating the sulfate solids and introducing the other acids (as in Examples 25-28 and 31-36). If it is desired to recover such salt in solid form, the alcohol may be evaporated off (preferably under vacuum) or may be precipitated by the addition of a non-solvent for the salt such as a hydrocarbon. It is contemplated that such further reaction of hydroxylamine may be conducted prior to separating the by-product sulfate. In such case, as free hydroxylamine becomes available in the alcoholic solution, it reacts with ketone or aldehyde (provided that the proper pH is reached). Reaction of alcoholic hydroxylamine with a mineral acid (inorganic acid) is preferably, however, conducted only after the by-product sulfate salt is removed. Organic acids, giving products which are in the liquid phase, are preferably reacted before removing the sulfate, but recovered from alcohol solvent after removing the solid sulfate phase. A convenient form of organic acid used in these instances is the ammonium or alkali metal salt of the organic acid.

Such salts may be hydrated but is preferably not. With anydrous salts, as with alkoxides, no water of neutralization is formed. In making organic hydroxylammonium salts, especially, it is also preferred that substantially no water be introduced into the reaction mixture with the alcohol: preferably the water:alcohol ratio is 0.05:1 or less, more preferably 0.01:1 or less and most preferably 0.001:1 or less. In general the only water added with the alcohol is that forming an azeotrope with recycled alcohol. In such event, especially if anhydrous alkoxides or organic salts are used, the water content of the product liquid phase will be particularly low and, therefore, the sulphate level in the hydroxylammonium salt produced will be very low.

The step of removing the by-product solid sulfate from the alcoholic solution containing hydroxylamine values may be carried out using any conventional technique for separating a solid from a liquid. Centrifugation, filtration, decantation and other conventional engineering steps are included. It is preferred that the recovered solid be washed with a solvent (such as the alcohol used for the solution) to remove adhered hydroxylamine-containing alcohol. Thereafter the solid may be dried, washed or recrystallized, treated in other ways to recover unreacted hydroxylammonium sulfate, or disposed of as initially separated.

The hydroxylammoneum salt now in alcohol solution can be recovered or transferred to aqueous media in a variety of ways. Simple evaporative crystallization will produce solid salt of reasonably high purity, and recrystallization may be used to improve purity. The solid salt may then be redissolved in water in selected amounts to produce aqueous solutions of desired concentrations. For salts which are unstable in concentrated form (e.g. the perchlorate or nitrate), wate can be added to the alcoholic solution, followed by evaporative concentration. In such event, the alcohol evaporated off (for recycle to step a) may be an azeotrope, which is approximately 1% water for methanol, approximately 4% water for ethanol and approximately 15% water for isopropanol. These azeotropes can be broken by conventional techniques if a lower water level is desired for step a (so as to produce lower sulfate levels in the product).

The present invention is illustrated by the following Examples, which are not intended to limit the invention:

EXAMPLE 1

A solution of methanolic sodium hydroxides was prepared by mixing sodium hydroxide pellets (17.2 g; 0.43 mol) with absolute methanol (150 mL) in a 250 mL Erlenmeyer flask.

In the meantime a 500 mL 3-necked flask was fitted with a thermometer, dropping funnel and nitrogen inlet (inert atmosphere) and a magnetic stirring bar (PTFE-coated, 1-½ inches or 3.8 cm long) was placed in it. Solid hydroxylamine sulfate (35 g; 0.213 mol) was placed in the flask with methanol (50 mL) and the flask was placed in an ice-water bath over a stir plate. With vigorous stirring, the methanolic NaOH solution was added slowly (over 5 minutes) using the dropping funnel, maintaining the reaction mixture temperature below 10° C. After the addition was complete, stirring was continued for 1-½ hours more with cooling (5°-10° C). A white slurry resulted and this is filtered over a Buchner funnel and the cake was washed with more methanol (25 mL). The clear and colorless filtrate (pH 12.5) was analyzed for free hydroxylamine by mixing with known excess of methyl ethyl ketone (MEK) (40 g) and adjusting the pH to 7 with concentrated $H_2SO_4$ (2.5 g). Methyl ethyl ketoxime formed was determined by gas chromatography to correspond to free hydroxylamine (87.4% yield).

The white filter cake (34.2 g) of sodium sulfate was analyzed for remaining hydroxylamine sulfate by dissolving in water (150 mL) and mixing with excess of MEK (40 g) and titrating with 50% NaOH solution (3.9 g) to pH 7. The amount of hydroxylamine sulfate left in the cake represented 11.4% of the total.

EXAMPLES 2-18

With the variations in reagents and conditions shown in Table 1, Example 1 was repeated, with the results (expressed as percentage of hydroxylamine values fed present in the solution and in the filter cake) as indicated in Table 1. The details of these examples are set forth in U.S. Ser. No. 437,920, the disclosure of which is incorporated herein by reference.

TABLE 1

| Example | Base | Solvent | Temperature | Time (hours) | Yield (%) | % In Cake |
|---|---|---|---|---|---|---|
| 1 | NaOH | MeOH | 5–10° C. | 1.5 | 87.4% | 11.4% |
| 2 | NaOH | MeOH | 22–25° C. | 2 | 71.2% | — |
| C3 | NaOH | MeOH | 35–40° C. | 1.5 | 18.8% | 76.5% |
| 4 | NaOH | MeOH | 5–10° C. | 6 | 90.7% | 0.9% |
| 5 | NaOH | MeOH then | 10° C. 22° C. | 6 12 | 80.5% | trace |
| 6 | NaOH | MeOH | <10° C. | 4 | 91.6% | 7.6% |
| 7* | NaOH | MeOH | 5° C. | 4 | 82.1% | 17.3% |
| 8** | NaOH | MeOH | 5–10° C. | 1.5 | 86.6% | 10.4% |
| 9* | NaOH | MeOH | 7–10° C. | 1 | 78.3% | 12.2% |
| 10** | NaOH | MeOH | 5–10° C. | 2 | 70.8% | 27.9% |
| 11 | NaOH | EtOH | 5–10° C. | 3 | 88.3% | 4.7% |
| 12 | NaOH | EtOH | 22–25° C. | 3 | 89.1% | 2.9% |
| 13 | LiOH*** | MeOH | 10° C. | 1.5 | 45.8% | 42.6% |
| 14 | LiOH*** | MeOH | 22–24° C. | 3 | 53.8% | 13.1% |
| C15 | KOH | MeOH | 10° C. | 3 | <1% | almost all |
| C16 | KOH | MeOH | 22–25° C. | 1 | <5% | almost all |
| 17 | KOH | EtOH | 22–25° C. | 3 | 77.9% | 16.6% |
| 18 | KOH | EtOH | 5–10° C. | 3 | 70.0% | 24.1% |

*The indicated examples used larger molar amounts of at least one reagent and/or larger volumes of alcohol solvent as follows:

| Example | Base (mol) | Total Alcohol | HS(mol) |
|---|---|---|---|
| 7 | NaOH 2.58 | MeOH 978 mL | 1.28 |
| 9 | NaOH 0.86 | MeOH 288 mL | 0.213 |

**The indicated examples used other variations from Example 1 as follows:
Example 8 - solid HS was added to 0.43 mol of NaOH dissolved in 200 mL methanol over 20 minutes with stirring.
Example 10 - 0.43 mol of NaOH was dissolved in 150 mL of methanol and 7.5 mL of water;
***LiOH.H₂O

EXAMPLE 19

In a 500 mL resin flask fitted with an overhead stirrer was placed hydroxylamine sulfate (35 g; 0.213 mol) mixed with methanol (200 mL) and water (10 mL). To the slurry (pH 4.2) was bubbled ammonia gas from a cylinder till the pH rose to 9.0 with stirring and cooling in water bath. At the end of one hour stirring pH had dropped to 6.6. More ammonia was introduced (pH 9.0) and stirring continued. This was repeated several times over a total of 3 hours. Finally, when the pH did not change after bringing up to 9.5 and stirring over 15 minutes, the slurry was filtered and the clear filtrate analyzed. The hydroxylamine content in the filtrate was determined to be 46.7% of theoretical yield.

The white filter cake after dissolving in water was analyzed and found to contain 42.4% of the original hydroxylamine sulfate started with.

COMPARATIVE EXAMPLE 20

Ammonia gas was dissolved in absolute methanol and a solution containing 11.6% NH₃ was prepared. Portion of this solution (88 g = 10.2 g NH₃) was added to a slurry of hydroxylamine sulfate (35 g; 0.213 mol) in methanol (100 mL) in a 500 mL 3-neck flask provided with magnetic stirring bar. The flask was cooled in ice water bath (5°–10° C.) and the slurry was stirred vigorously for 3 hours. It was filtered and the cake washed with methanol to furnish a solution (176 g). This clear solution was analyzed potentiometrically and found to contain 17.1% yield of hydroxylamine.

The white solid (33 g) was dissolved in water and analyzed and found to contain 78.5% hydroxylamine sulfate still present unused.

COMPARATIVE EXAMPLE 21

Ammonia solution in methanol (100 g = 11.7 g NH₃) was added to hydroxylamine sulfate (35 g; 0.213 mol) and methanol (100 mL) in a 500 mL autoclave and the reactor quickly sealed. The contents were stirred for 3 hours with cooling at 10°. No pressure development was noticed throughout.

The slurry was filtered and the cake washed with methanol. The total filtrate (263 g) on analysis potentiometrically showed the presence of free hydroxylammonium corresponding to 10.0% of theoretical. The crude solid (32.5 g) contained 82.8% of unused hydroxylamine sulfate.

COMPARATIVE EXAMPLE 22

In a 500 mL autoclave was placed solid hydroxylamine sulfate (35 g; 0.213 mol) mixed with methanol (50 mL) and a solution of ammonia in methanol (150 g of 7.4% solution = 11.1 g NH₃) was added quickly and the autoclave sealed. The contents were heated (40°–50° C.) and stirred very vigorously for 2 hours. Slight pressure development was noticed during the heating, but the pressure disappeared as it was cooled to ambient temperature.

The contents were filtered and a colorless filtrate (196 g) collected along with white solid (32 g). The filtrate was analyzed potentiometrically and found to contain 5.7% yield of hydroxylamine. The solid contained 84.0% of unreacted hydroxylamine sulfate.

COMPARATIVE EXAMPLE 23

The same 500 mL autoclave as in previous example was used. A solution of NH₃ in ethanol (150 g, 5.7% = 8.55 g NH₃) was added quickly to hydroxylamine sulfate (35 g; 0.213 mol) and ethanol (50 mL) in the autoclave. After sealing the reactor, it was stirred at ambient temperature (19° C.) for 3 hours.

On filtration of the contents and washing with ethanol, a clear, colorless liquid (232 g) was collected which on analysis as usual showed 13.9% yield of free hydroxylammonium. The solid (32 g) contained hydroxylamine sulfate corresponding to 76.7% of the amount started with.

COMPARATIVE EXAMPLE 24

In a 500 mL 3-neck flask was placed hydroxylamine sulfate (35 g; 0213 mol) and solution of sodium hydroxide pellets (17.2 g; 0.43 mol) in ethylene glycol (300 g) was added with stirring using a magnetic stirring bar. Stirring was continued over a total of 3 hours, first 2 hours at room temperature and the last hour at 30° C.

After filtering the viscous slurry, the filtrate was analyzed potentiometrically and was found to have hydroxylamine equal to 7.4% yield. The white solid (32 g) was analyzed and found to contain 75.3% of the original hydroxylamine sulfate.

PREPARATION OF HYDROXYLAMMONIUM SALTS

The preparation of salts from alcoholic hydroxylamine solutions are illustrated in the following examples:

| Example | salts | |
|---|---|---|
| 25 | Hydroxylammonium | Chloride |
| 26 | " | Nitrate |
| 27 | " | Phosphate |
| 28 | " | Oxalate |
| 31 | " | Acetate |
| 32 | " | Acetate |
| 33 | " | Benzoate |
| 34 | " | Formate |
| 35 | " | Formate |
| 36 | " | Perchlorate |
| 37 | " | Acetate |
| 38 | " | Acetate |

EXAMPLE 25

In a 500 mL 3-necked flask was placed hydroxylamine sulfate (70 g; 0.43 mol) with methanol (50 mL). To this was added with stirring using magnetic stirring bar a solution of NaOH pellets (34.4 g; 0.86 mol) in methanol (300 mL) over 15 minutes with cooling in an ice-water bath. Stirring was continued over 3 hours at temperatures ranging from 2° to 7° C. The pH of the slurry was recorded (11.2) and conc. $H_2SO_4$ (1.5 g) was added dropwise until pH 8.0 was reached.

The white slurry was filtered and the cake washed on the filter with more methanol. The total filtrate (323 g) was analyzed potentiometrically and found to contain free hydroxylamine corresponding to 85.2% of the starting sulfate.

The filtercake (69 g) was analyzed for hydroxylamine sulfate left behind (10.9%).

The methanolic solution of hydroxylamine was placed in a 500 mL Erlenmeyer containing a magnetic stirring bar and the flask in turn was placed in an ice bath over a stir place. HCl gas was slowly bubbled into the solution with stirring and maintaining the temperature at 20°-25° C. HCl addition was continued until the pH dropped from 8.0 to 2.8. The solution was then placed in a 1 liter round bottom flask and evaporated to dryness under reduced pressure. White crystalline solid of hydroxylamine hydrochloride (49.9 g) was collected (M.P. 154.5° C.) yield 84.1%.

EXAMPLE 26

A solution of sodium methoxide in methanol produced by dissolving sodium (10 g; 0.435 mol) in methanol (150 mL) was stirred with hydroxylamine sulfate (35 g; 0.213 mol) in ice-water bath (5°-10° C.) over 2 hours. The slurry filtered and the clear methanolic filtrate with cake-wash (pH 9.2) was mixed with conc. $H_2SO_4$ (0.8 g) to pH 8.0. The thin white solid produced was filtered off and the clear filtrate was placed in 500 mL Erlenmeyer with a magnetic stirring bar. While cooling in icewater bath and stirring, conc. $HNO_3$ (35.5 g) was added till the pH reached 2.8. The clear methanolic solution of hydroxylamine nitrate (273.3 mL) was found to contain 37.99 g $NH_2OH.HNO_3$ (13.9 g in 100 mL). Overall yield 92.7%.

EXAMPLE 27

A solution of hydroxylamine in methanol prepared as in Example 7 was used. The solution (100 mL containing 4.84 g $NH_2OH$) was placed in a 250 mL 3-neck flask fitted with thermometer and a dropping funnel and containing a magnetic stirring bar. With stirring and cooling in an ice-water bath (5° C.) 85% orthophosphoric acid (8.0 g; 0.069 mol) was slowly added until the pH of the solution dropped from 11.8 to 8.0, and a bulky white slurry was produced. After stirring at 5° C. for 15 minutes more, the solid was collected by filtration (11.8 g crude cake). It was recrystallized from hot water, and white crystalline hydroxylammonium phosphate (8.2 g on drying) was collected. Yield 85.4% (M.P. 175° C. with decomposition).

EXAMPLE 28

A solution of hydroxylamine in methanol (680 mL) as in Example 27 as used (pH 11.8). Conc. $H_2SO_4$ was slowly added to adjust the pH to 8.0 and the thin white precipitate formed was filtered off and the clear filtrate placed in a 1 liter Erlenmeyer flask. A magnetic stirring bar was introduced and the flask was placed in an ice-water bath. Oxalic acid (45 g; 0.5 mol) dissolved in methanol (100 mL) was slowly added with cooling and stirring. A thick white slurry was produced and this was filtered and the crude white solid (84.8 g) was collected. A portion (25 g) of this solid was recrystallized from hot water to produce white crystalline hydroxylammonium oxalate (M.P. 192° C. with decomposition). Yield 94.6%.

EXAMPLE 29

A 500 mL 3-necked flask was fitted with a thermometer, reflux-condenser and drying tube. Freshly cut sodium (10.0 g; 0.435 mol) was placed in the flask and absolute methanol (175 mL) was carefully added with cooling. After the sodium was completely dissolved in methanol forming a clear solution of sodium methoxide, solid hydroxylamine sulfate (35 g; 0.213 mol) was added with cooling over 2 minutes. No significant exotherm was noticed. The mixture was stirred with cooling (10° C.) in ice- water bath using a magnetic stirring bar over a stir plate for one hour. Subsequently, cooling was removed and vigorous stirring continued at ambiemt temperature for 2 hours more. By this point a white slurry had formed, and this was filtered and the cake washed using more methanol. The total filtrate (162 g) was analyzed potentiometrically and found to contain hydroxylamine corresponding to 87.5% yield. The filtrate was virtually free of water ($<0.5\%$ $H_2O$).

The white solid (32 g) was dissolved in water and analyzed for unused hydroxylamine sulfate (1.6%).

COMPARATIVE EXAMPLE 30

In a 500 mL 3-necked flask was fitted with thermometer, reflux condenser, and drying tube was placed absolute methanol (100 mL) and freshly-cut potassium (8.4 g; 0.215 mol) was added piece-by-piece with cooling in ice-bath and a clear solution of potassium methoxide in methanol was produced. To this solution was added with vigorous stirring crystalline hydroxylamine sulfate (17.5 g; 0.107 mol) and stirring was continued at ambient temperature for 3 hours. No noticeable change (no milkiness) was found to be developing.

The slurry was filtered and the filter cake was washed with more methanol. The total filtrate (125 g) was analyzed potentiometrically and found to contain virtually no hydroxylamine (<0.3% yield). The crude filter cake (18 g) which appeared crystalline (similar to the starting hydroxylamine sulfate) was dissolved in water (75 mL) and analyzed and found to contain over 95% of the starting hydroxylamine sulfate.

EXAMPLE 31

Preparation of Hydroxylammonium Acetate.

A 2 liter 3-neck flask with baffles was fitted with thermometer, overhead agitator and a dropping funnel. A mixture of solid hydroxylamine sulfate (210 g, 1.28 mol) and absolute methanol (400 mL) was placed in the flask and vigoriously agitated with cooling in ice bath (0°–5° C.). A solution of sodium hydroxide pellets (103 g; 2.58 mol) in absolute methanol (700 mL) was slowly added using the dropping funnel. The slurry was stirred vigorously over 7 hours with continued cooling; and concentrated $H_2SO_4$ (5.8 g) was added to adjust the pH to 8.8. The white slurry was filtered and the clear filtrate (1165 mL) analyzed (potentiometric titration) and found to contain 5.99 g of hydroxylamine per 100 mL of the solution.

In a 1 liter Erlenmeyer flask provided with a PTFE-coated magnetic stirring bar was placed a portion (690 mL) of the methanolic hydroxylamine solution. With cooling in ice-water bath (5°–10°C.) and stirring glacial acetic acid (75 g; 1.25 mol) was slowly added over 20 minutes. The clear solution (pH 5.6) was then stirred at ambient temperature for 1 hour and was evaporated on the rotovap to remove methanol under reduced pressure. A colorless and very viscous liquid was obtained (116 g), which on standing crystallized into a white crystalline solid. Yield (99.5%)

EXAMPLE 32

Preparation of Hydroxylammonium Acetate

A hydroxylamine solution in methanol prepared as in example 31 containing 4.1 g $NH_2OH$ per 100 mL of solution was used. Glacial acetic acid (30 g; 0.43 mol) was diluted with distilled water (30 g) and this 50% aqueous acetic acid was added slowly with stirring (magnetic stirring bar) and cooling (ice bath) to the hydroxylamine solution (350 mL; 0.43 mols $NH_2OH$) in a 500 mL Erlenmeyer flask. The pH was 5.6. The clear solution was carefully evaporated to remove methanol and an aqueous solution of hydroxylamine acetate (75 g) of approximately 60% concentration was obtained in excellent yield as a colorless liquid.

EXAMPLE 33

Preparation of Hydroxylammonium Benzoate

A solution of hydroxylamine in methanol prepared as in example 31 was used (4.1 g $NH_2OH$ in 100 mL solution). The hydroxylamine solution (41 mL) was placed in a 250 mL Erlenmeyer flask furnished with magnetic stirring bar and was kept cooled in ice-water bath (about 10° C.). The pH was 7.6. A solution of benzoic acid (6.1 g; 0.05 mol) in absolute methanol (50 mL) was slowly added with stirring (pH 6.3). The clear mixture was then stirred for one hour at room temperature and then carefully evaporated to dryness. Hydroxylamine benzoate was collected as a white crystalline solid (7.5 g). Yield 96.8%.

EXAMPLE 34

Preparation of Hydroxylammonium Formate

A methanolic solution of hydroxylamine (820 mL; at 5.56 g/100 mL) prepared as in example 31 was placed in a 2 liter Erlenmeyer flask furnished with a magnetic stirring bar. This was kept cooled in ice-water bath (about 10° C.) with stirring and a solution of formic acid (63.8 g; 1.38 mol) in distilled water (77 g) was slowly added. After completion of addition it was stirred further for an hour without cooling and then transferred to a 2 liter round bottom flask and the methanol carefully evaporated off on a rotary evaporator. A clear and colorless solution of aqueous hydroxylamine formate was collected (177.5 g; 61% solution).

EXAMPLE 35

Preparation of Hydroxylamminium Formate

A solution of hydroxylamine in methanol, prepared as in example 31, containing 4% of $NH_2OH$ (potentiometric titration) was used. A 500 mL Erlenmeyer flask containing a PTFE-coated magnetic stirring bar was placed in an ice bath and the hydroxylamine solution (225 mL) was added to it with stirring (temp. 5° C.). Formic acid (14.5 g; 0.31 mol) was then added slowly to it. Temperature rose to 20° C. by the end of the addition (pH 5). The clear solution was stirred for one half-hour more without cooling and then evaporated under reduced pressure (rotovap) in a 500 mL round bottom flask. A white crystalline solid was collected (19.8 g; yield 92.8%; M.P. 74°–75° C.).

EXAMPLE 36

Preparation of Hydroxylammonium Perchlorate

A solution of 50% perchloric acid in water was prepared by mixing 70% perchloric acid (Fisher Scientific) with distilled water.

A methanolic hydroxylamine solution (300 mL; at 5.27 g in 100 mL solution) was placed in a 500 mL Erlenmeyer flask and it was cooled in ice bath with stirring using a magnetic PTFE-coated stirring bar. The perchloric acid solution was slowly added (99 g of the 50% solution) to pH 3.15. After stirring further for one half hour at room temperature, the clear solution was transferred to a 500 mL round bottom flask and the methanol carefully distilled off under reduced pressure (rotovap) without any heating. A clear liquid (112.5 g) was collected which was analyzed by potentiometric titration to be 56% solution of hydroxylammonium perchlorate (yield 98.5%).

EXAMPLE 37

In a 250 mL 3-neck flask furnished with thermometer, dropping funnel and magnetic stirring bar was placed hydroxylamine sulfate (4.1 g; 0.025 mol) and absolute methanol (50 mL). The slurry was stirred with cooling in ice bath (5° C.). A solution of sodium acetate trihydrate (6.8 g; 0.05 mol) in methanol (80 mL) was then slowly added. The solution (pH 7.2) was stirred for 3 hours at about 5° C. The pH was 6.5. The fine white solid of sodium sulfate was filtered off and the clear filtrate evaporated to dryness under reduced pressure. A white crystalline solid (4.5 g) of hydroxylammonium acetate was collected; mp 83°–85° C.

EXAMPLE 38

A 250 mL 3-neck flask was fitted with thermometer, dropping funnel and a drying tube and a PTFE-coated magnetic stirring bar was placed in it. Hydroxylamine sulfate (4.1 g; 0.025 mol) with methanol (50 mL) was added to the flask and stirred with cooling in ice bath. A solution acetate solution prepared by dissolving anhydrous sodium acetate (4.1 g; 0.05 mol) in absolute methanol (80 mL) was added from the dropping funnel slowly. The solution was then stirred cold for 3 hours and the fine white solid filtered off. The clear filt rate on evaporation to dryness furnished hydroxylammonium acetate as a white crystalline solid (4.6 g): m.p. 84°–85° C.

Comparative Example 39

In a 250 mL neck flask fitted with dropping funnel, thermometer and reflux condenser was placed hydroxylamine sulfate (4.1 g; 0.025 mol) mixed with absolute methanol (50 mL). The mixture was kept stirred vigourously using a magnetic stirring bar and a solution of anhydrous sodium acetate (4.1 g; 0.05 mol) in absolute methanol (80 mL) was added to it. Then the mixture was heated at 50° C. for 3 hours with continued stirring.

On cooling to ambient temperature the slurry was filtered and the clear filtrate analyzed potentionmetrically for hydroxylamine value. It was found to contain 46.4% of the theoretical amount of hydroxylamine. The solid on the filter appeared granular (unlike in examples 37 and 38) resembling the starting hydroxylamine sulfate, suggesting that the reaction was imcomplete.

What is claimed is:

1. A process comprising the steps of:
   (a) reacting an alcoholic solution of a base selected from the group consisting of sodium hydroxide, potassium hydroxide, lithium hydroxide, ammonium hydroxide and the corresponding alkoxides of 1–5 carbons with solid hydroxylammonium sulfate, employing an alcohol of 1–3 carbons, a temperature, a pressure and a time sufficient to produce a liquid phase having at least 50% of the hydroxylamine values of the hydroxylammonium sulfate,
   (b) separating the solid phase comprising a sulfate salt corresponding to said base from the liquid phase, and
   (c) reacting the separated liquid phase with an acid other than sulfuric acid to produce an hydroxylammonium salt other than hydroxylammonium sulfate.

2. The process of claim 1 wherein said base is sodium hydroxide.

3. The process of claim 2 wherein the alcohol is methanol.

4. The process of claim 2 wherein the alcohol is ethanol.

5. The process of claim 2 wherein the reacting step (a) is conducted at a temperature not greater than about 30° C.

6. The process of claim 3 wherein the reacting step (a) is conducted at a temperature not greater than about 20° C.

7. The process of claim 6 wherein the reacting step (a) is conducted at a temperature not greater than about 10° C.

8. The process of claim 1 wherein said base is potassium hydroxide.

9. The process of claim 8 wherein the alcohol is ethanol.

10. The process of claim 9 wherein the reacting step (a) is conducted at a temperature between about 10° C. and about 40° C.

11. The process of claim 10 wherein the reacting step (a) is conducted at a temperature between about 5° C. and about 25° C.

12. The process of claim 1 wherein said base is lithium hydroxide.

13. The process of claim 1 wherein said base is an alkoxide.

14. The process of claim 13 wherein the base is sodium methoxide and the solvent is methanol.

15. The process of claim 13 wherein the base is sodium ethoxide or potassium ethoxide and the solvent is ethanol.

16. The process of claim 1 wherein said separating step (b) comprising separating a free hydroxylamine solution in alcohol of pH between about 7 and about 12 from a solid phase comprising said sulfate salt corresponding to said base.

17. The process of claim 1 wherein the acid is an alkanecarboxylic or dicarboxylic acid and the product solution is an alcoholic solution of an hydroxylammonium alkanecarboxylate or dihydroxyammonium alkanedicarboxylate.

18. The process of claim 17 wherein said other acid is formic acid.

19. The process of claim 17 wherein said other acid is acetic acid.

20. The process of claim 17 wherein said other acid is oxalic acid.

21. The process of claim 1 wherein said other acid is a mineral acid.

22. The process of claim 21 wherein the other acid is HCl and the product solution is alcoholic hydroxylammonium chloride.

23. The process of claim 21 wherein said other acid is nitric acid and the product solution is an alcoholic solution of hydroxylammonium nitrate.

24. The process of claim 21 wherein said other acid is perchloric acid and the product solution is an alcoholic solution of hydroxylammoninum perchlorate.

25. A process comprising the steps of:
   (a) reacting an alcoholic solution of a base or basic organic salt selected from the group consisting of sodium hydroxide, potassium hydroxide, lithium hydroxide, ammonium hydroxide, the corresponding alkoxides of 1–5 carbons and the corresponding organic salts with solid hydroxylammonium sulfate and, in the case of base, an organic acid, in the substantial absence of adder water or water introduced with the alcohol; employing an alcohol of 1–3 carbons, a temperature not greater than about 30° C., a pressure and a time sufficient to produce a liquid phase having at least 50% of the hydroxylamine values of the hydroxylammonium sulfate and a solid alkali metal or ammonium sulfate corresponding to the base or basic salt; and
   separating the solid phase comprising sulfate salt from a liquid phase containing an organic hydroxylammonium salt corresponding to said basic organic salt or organic acid, said liquid phase being substantially free of sulfate.

26. The process of claim 25 wherein said base is sodium hydroxide or said basic salt is a sodium salt.

27. The process of claim 26 wherein said alcohol is methanol.

28. The process of claim 27 wherein said temperature is not greater than about 20° C.

29. The process of claim 28 wherein said temperature is not greater than about 10° C.

30. The process of claim 28 wherein said basic salt is a sodium alkanecarboxylate, a disodium alkanedicarboxylate, sodium benzoate or sodium aryl or alkylaryl sulfonate.

* * * * *